United States Patent
Schumann et al.

(10) Patent No.: US 7,767,644 B2
(45) Date of Patent: Aug. 3, 2010

(54) ERYTHROPOIETIN LIQUID FORMULATION

(75) Inventors: Christof Schumann, Breitscheid-Erdbach (DE); Jan-Ole Hesse, Bad Nauheim (DE)

(73) Assignee: Bioceuticals Arzneimittel AG, Bad Vilbel (DE)

( * ) Notice: Subject to any disclaimer, the term of this patent is extended or adjusted under 35 U.S.C. 154(b) by 0 days.

(21) Appl. No.: 10/592,241

(22) PCT Filed: Mar. 10, 2005

(86) PCT No.: PCT/EP2005/002551

§ 371 (c)(1),
(2), (4) Date: Jul. 10, 2007

(87) PCT Pub. No.: WO2005/087804

PCT Pub. Date: Sep. 22, 2005

(65) Prior Publication Data

US 2008/0039371 A1 Feb. 14, 2008

(30) Foreign Application Priority Data

Mar. 10, 2004 (DE) .................. 10 2004 011 663

(51) Int. Cl.
*A61K 38/18* (2006.01)
*C07K 14/505* (2006.01)
(52) U.S. Cl. .................................. 514/8; 530/397
(58) Field of Classification Search ............... None
See application file for complete search history.

(56) References Cited

U.S. PATENT DOCUMENTS

| 6,120,761 A | 9/2000 | Yamazaki et al. |
| 6,696,056 B1 * | 2/2004 | Cheung et al. ............. 424/85.1 |
| 6,908,610 B1 * | 6/2005 | Sato ......................... 424/85.1 |
| 7,109,161 B1 * | 9/2006 | Gayed ........................... 514/2 |
| 2002/0037841 A1 | 3/2002 | Papadimitriou |
| 2003/0162711 A1 | 8/2003 | Bjorn et al. |
| 2004/0022792 A1 | 2/2004 | Klinke et al. |

FOREIGN PATENT DOCUMENTS

| DE | 198 56 443 A1 | 6/2000 |
| EP | 0 178 665 | 4/1986 |
| EP | 0 306 824 | 3/1989 |
| EP | 0 909 564 A1 | 4/1999 |
| WO | WO 91/04743 A1 | 4/1991 |
| WO | WO 00/51629 * | 9/2000 |
| WO | WO 00/61169 | 10/2000 |

* cited by examiner

*Primary Examiner*—Marianne P Allen
*Assistant Examiner*—Regina M DeBerry
(74) *Attorney, Agent, or Firm*—Knobbe Martens Olson & Bear LLP

(57) ABSTRACT

The invention relates to erythropoietin liquid formulations that are stable in storage and to a method for the production thereof. The invention particularly relates to erythropoietin liquid formulations, which contain at least four amino acids selected from the group consisting of leucine, isoleucine, threonine, glutamic acid, aspartic acid and phenylalanine, and in which the addition of preservatives, urea or human serum albumine can be foregone.

8 Claims, No Drawings

ERYTHROPOIETIN LIQUID FORMULATION

CROSS REFERENCE TO RELATED APPLICATION

This application claims the benefit and priority to and is a U.S. National Phase of PCT International Application Number PCT/EP2005/002551, filed on Mar. 10, 2005, designating the United States of America, which claims priority under 35 U.S.C. §119 to German Application Number 10 2004 011 663.6 filed on Mar. 10, 2004. The disclosures of the above-described applications are hereby incorporated by reference in their entirety.

The present invention relates to storage stable liquid erythropoietin formulations and methods for their preparation. In particular, the present invention relates to liquid erythropoietin formulations, which contain at least four amino acids selected from the group consisting of leucine, isoleucine, threonine, glutamic acid, aspartic acid and phenylalanine, and wherein the addition of preservatives, urea or human serum albumin can be omitted.

Erythropoietin, shortly referred to as EPO, is a glycoprotein stimulating the production of erythrocytes in the bone marrow. EPO is mostly produced in the kidneys and from there reaches its destination via the blood circulation. In the case of renal failure, the damaged kidneys do not produce enough EPO or none at all, which causes that too few erythrocytes emerge from the stem cells of the bone marrow. This renal anemia can be treated by means of administering EPO in physiological quantities, which stimulate the production of erythrocytes in the bone marrow. The EPO used for administration can be obtained either from human urine or by means of gene technological methods. Since EPO is contained in the human body only in small traces, isolating EPO from its natural source for therapeutical applications is almost impossible. Thus, gene technological methods offer the only economic possibility of producing said substance in larger quantities.

Recombinant production of erythropoietin is possible since the identification of the human erythropoietin gene in the year 1984. Since the early 90s, various pharmaceuticals have been developed, which contain human erythropoietin produced in a gene technological manner in eukaryotic cells, in particular in CHO (Chinese Hamster Ovary) cells. The production of recombinant human erythropoietin is, for example, described in EP-A-0 148 605 and EP-A-205 564.

EPO is conventionally formulated in liquid form and is as such injected intravenously or subcutaneously. However, problems with respect to stability arise in the liquid formulation of EPO. Said problems can possibly be attributed to a destruction of the erythropoietin molecules by catalytic effects of the surface of the containers serving for storage. It is furthermore presumed that adsorption of the EPO molecules to the container wall takes place, which leads to a loss of protein and activity. In the past, different approaches have thus been pursued in order to stabilize liquid formulations of EPO by means of adding various substances. Among these stabilizing compounds are, for example, polymeric substances like polyethylene glycol, dextrans and gelatin as well as various sugars and sugar alcohols, inorganic salts, and thiol compounds. Serum proteins like human serum albumin (HSA) are also often added. However, from an allergenic and immunological point of view the use of said serum proteins is not desirable.

In EP-A-0 306 824, the use of various amino acids as stabilizers in EPO formulations is described, wherein the amino acids are used together with urea in order to stabilize EPO. Furthermore; storage of the formulations described in EP-A-0 306 824 is not carried out in liquid form but in form of a lyophilisate, which is reconstituted with water directly before use.

In EP-A-0 607 156, EPO formulations are described, which are stable and possess shelf life due to the presence of a preservative.

It is an object of the present invention to produce a storage stable EPO preparation, which can be stored over a longer period in liquid form and which does not require additives like HSA, urea or preservatives. In this manner, a stable liquid EPO formulation is to be provided, which preferably avoids any risk with respect to tolerability of the formulation.

According to the present invention, this problem is solved by the subject matter of claim 1. Preferred embodiments are defined in the subclaims.

It has been found that, even in the absence of HSA, urea or polymeric stabilizing agents, EPO compositions containing a specific combination of amino acids can be stored under stable conditions in liquid form for a longer time without suffering a significant loss in stability.

Thus, the present invention relates to a storage stable liquid erythropoietin formulation, which
(i) contains at least four amino acids selected from the group consisting of leucine, isoleucine, threonine, glutamic acid, aspartic acid, and phenylalanine,
(ii) is free of preservatives, urea, and serum proteins, and
(iii) has not been reconstituted from a lyophilisate.

A particularly preferred embodiment additionally contains the amino acid glycine.

The liquid formulation according to the present invention not only offers the advantages that it does not require potentially immunogenic compounds and that it contains, in total, a number of different classes of compounds which is as low as possible, but also that it does not require lyophilization at any stage of the production process. On the one hand, this saves the expenses connected with lyophilization, on the other hand the risks of mechanical problems are avoided, for example if the lyophilisate cannot be reconstituted in a complete or sufficient manner.

Within the scope of the present invention, the term "storage stable" is understood to denote that the content of active EPO molecules still amounts to 80% or more of the initial concentration after three months of storing the liquid EPO formulation at 25° C. Preferably, after storage for three months at 25° C., the remaining content of EPO activity still amounts to at least 85%, more preferably at least 90%, and most preferably at least 95% of the original activity. The activity of the erythropoietin can be determined by means of conventional activity tests, as they have already been described in the prior art for EPO; in addition, see also European Pharmacopoeia, 01/2002:1316 (4th edition).

Within the scope of the present invention, the term "liquid formulation" is understood to denote that the formulation of erythropoietin together with further substances contained in the formulation is not lyophilized at any stage of the production process, i.e. neither before nor during or after mixing the substances, and that the formulation is intended for intravenous or subcutaneous application as injection or infusion solution.

The formulation according to the present invention contains no amino acids other than leucine, isoleucine, threonine, glutamic acid, aspartic acid, phenylalanine or glycine. Preferably, the formulation contains no amino acids other than leucine, isoleucine, threonine, glutamic acid, phenylalanine and glycine. In particular, the EPO formulation according to the present invention does not contain any alkaline amino acids. Likewise, the formulation does not contain an aminoacetic acid. The strict absence of serum proteins or other stabilizing proteins, of urea and preservatives from the formulation according to the present invention has already been mentioned in the above.

In each case, the concentration of isoleucine and leucine, as far as these amino acids are contained in the formulation, is in the range of from 0.25 to 1.5 g/l, preferably 0.5 to 1.25 g/l, and particularly preferably it is 1.0 g/l.

The concentration of glutamic acid and aspartic acid, as far as said amino acids are contained in the formulation, is in the range of from 0.1 to 0.5 g/l, preferably 0.2 to 0.4 g/l, and particularly preferably 0.25 g/l.

The concentration of threonine, as far as this amino acid is contained in the formulation, is in the range of from 0.1 to 0.5 g/l, preferably 0.2 to 0.4 g/l, particularly preferably it is 0.25 g/l.

The concentration of phenylalanine, as far as this amino acid is contained in the formulation, is in the range of from 0.2 to 1.0 g/l, preferably 0.3 to 0.8 g/l, and particularly preferably 0.5 g/l.

The concentration of glycine in the formulation according to the present invention, as far as this amino acid is contained in the formulation, is in the range of from 2.0 to 10.0 g/l, preferably 5.0 to 8.0 g/l, and particularly preferably it is 7.5 g/l.

The erythropoietin suitable for the use in the formulations according to the invention is recombinant erythropoietin, which is produced in eukaryotic cells. Preferably, the recombinant erythropoietin is produced in mammalian cells, particularly preferably in CHO cells, as is described for example in EP-A-0 205 564 and EP-A-0 148 605. Subsequently to fermentation, which is performed according to conventional protocols, a purification step of the recombinant erythropoietin is conducted by means of chromatographic methods. Both fermentation and purification of the protein have also been described in the prior art, for example in EP-A-0 830 376. Purification of erythropoietin is also an object of EP-A-0 228 452, EP-A-0 428 267, and WO-A-03/045996. However, further conventional purification techniques and sequences of purification steps can also be employed.

Within the scope of the present invention, "erythropoietin" is understood to denote any protein, which is capable of stimulating erythrocyte production in the bone marrow and which can be unmistakably identified as erythropoietin according to the assay described in the European Pharmacopoeia (Ph. Eur.; 01/2002:1316) (Determination of the activity in polycythemic or normocythemic mice). The erythropoietin can be the wild-type human erythropoietin or a variant thereof having one or more amino acid substitutions, deletions, or additions. Likewise, the erythropoietin contained in the formulation according to the present invention can be a conjugate, in which the protein is present in conjugated form, for example with polymers like polyalkylene glycols, so-called PEGylated erythropoietin.

In a preferred embodiment, the formulation of this invention contains neither sugar nor sugar alcohols for stabilization. It is likewise preferred that the formulation does not contain polymeric compounds as stabilizing agents. Furthermore, the formulation is free of preservatives, wherein these are to be understood as substances, which are conventionally used as preservatives for increasing storage stability and which, in standard concentrations, have a bactericidal effect. In particular, the formulation does not contain preservatives like chloroethane, benzyl alcohol, p-chloro-m-cresol, and pyrocarbonic acid dialkyl ester, and benzalkonium chloride.

The pH of the formulation is not considerably higher than the pH of blood, i.e. preferably not higher than 7.4. Normally, the pH of the formulation lies between 6.0 and 7.4, preferably between 6.5 and 7.4, and particularly preferably between 7.0 and 7.4. If an adjustment in order to achieve the desired pH range is required, the pH value is adjusted by means of suitable solutions; with acidic solutions in case a reduction of the pH value is indicated and with alkaline solutions in case an increase of the pH value is indicated. Preferably, the pH is adjusted by means of HCl and NaOH, respectively.

For injection purposes, the use of pure water as solvent is preferred. Other solvents suitable and conventional for pharmaceutical preparations can also be employed, however.

The buffer in use can be any physiologically acceptable buffer, which allows for buffering at concentrations required for injection or infusion solutions within the pH range specified above. Suitable buffers are, for example, phosphate, citrate, carbonate, and HEPES. The use of a phosphate buffer is preferred. The buffer compound or compounds is/are employed at a concentration of about 20 to 100 mM, preferably 30 to 80 mM, and particularly preferably 40 to 60 mM.

In a preferred embodiment, the formulation according to the present invention contains a surfactant as additional component. The use of a detergent is supposed to reduce adsorption of EPO to the container walls. To this end, small quantities of a detergent are usually sufficient. Basically, any physiologically acceptable detergent can be employed within the scope of the present invention. Polyoxyethylene sorbitan alkylesters or sorbitan trioleate are particularly suitable, polyoxyethylene sorbitan alkylesters being particularly preferred. Preferably, the polyoxyethylene sorbitan alkylester is Polysorbate 20 and/or Poylsorbate 80, Polysorbate 20 being most preferred. The concentration of the detergent is in the range of from 0.01 to 1.0 g/l, preferably from 0.05 to 0.2 g/l, and most preferably it is 0.1 g/l.

In preferred embodiments, the formulation further contains small quantities of a physiologically acceptable complexing agent. Said complexing agent is, for example, a calcium salt, citrate, or EDTA. Within the scope of the present invention, salts containing calcium, like for example calcium chloride, are particularly preferred. The concentration of the calcium salt lies between 0.005 and 0.05 g/l, preferably between 0.008 and 0.012 g/l, and particularly preferably it is 0.01 g/l.

Any suitable salt can be employed for adjusting osmolality. For this purpose, the use of sodium chloride is preferred. Herein, the concentration of sodium chloride lies in a range of 0.5 to 2.5 g/l, preferably between 1.0 and 2.0 g/l, and particularly preferably between 1.3 and 1.6 g/l.

The osmolality of the liquid formulation is 200 to 400 mosmol/kg, preferably 250 to 300 mosmol/kg, and most preferably 260 to 290 mosmol/kg.

A preferred embodiment of the present invention provides a liquid EPO formulation containing, beside the active agent EPO, the amino acids leucine, isoleucine, threonine, glutamic acid, phenylalanine, and glycine as well as calcium chloride, polysorbate, phosphate buffer and sodium chloride, wherein further ingredients are not present.

The activity of the erythropoietin used should not lie below 100,000 IE/mg (see also European Pharmacopoeia, 01/2002: 1316 (4th edition)). Preferably, the EPO has an activity of at least 110,000 IE/mg, particularly preferably of at least 120,000 IE/mg.

The erythropoietin concentration depends on the active agent concentration, which is desired for the finished syringe in each case. Typical EPO concentrations lie between 1,500

IE/ml and 40,000 IE/ml, see for example the commercial products NeoRecormon® and Erypo® in German Red List 2004.

The components of the formulation are available from conventional sources, for example by the companies Sigma or Merck.

The production of the formulation can be performed according to methods conventional in the prior art.

The present invention also relates to a method for preparing the liquid EPO formulation of the present invention. Herein, the components of the formulation mentioned above are dissolved in an aqueous buffer. As discussed above, the aqueous buffer preferably is a phosphate buffer.

In a preferred embodiment of the method according to the present invention for preparing the liquid formulation, first the solvent, preferably water for injection purposes, is provided and subsequently sodium dihydrogenphosphate dihydrate and disodiumhydrogenphosphate dihydrate as buffers, calcium chloride, sodium chloride, and the amino acids used, preferably being glycine, leucine, isoleucine, threonine, glutamic acid, and phenylalanine, are dissolved in the solvent. After total dissolution of the components, a solution of polysorbate (in the respective solvent) is added. Finally, a solution of erythropoietin (in the respective solvent) is added in the next step.

During preparation and at the end of preparation, the pH of the solution is determined and adjusted, if necessary, to be in a range of from 7.0 to 7.4 using suitable solutions, in particular NaOH or HCl.

Finally, the finished liquid formulation is filled into a suitable container, where it is stored until application. Said container is, in particular, a finished syringe, a pierceable stopper flask, or an ampoule.

The following Examples are intended to illustrate the invention without limiting its scope.

EXAMPLES

1. Liquid Erythropoietin Formulation

Preparation of a Liquid Formulation of Erythropoietin Having an Agent Concentration of 3,333 IE/ml.

| Component | Content per finished syringe | |
| --- | --- | --- |
| EPO | 3,333 | IE/ml |
| Polysorbate 20 | 0.1 | mg |
| Sodium dihydrogenphosphate dihydrate | 1.43 | mg |
| Sodium monohydrogenphosphate dihydrate | 5.6 | mg |
| $CaCl_2 \times 2 H_2O$ | 0.01 | mg |
| Glycine | 7.5 | mg |
| Leucine | 1.0 | mg |
| Isoleucine | 1.0 | mg |
| Threonine | 0.25 | mg |
| Glutamic acid | 0.25 | mg |
| Phenylalanine | 0.5 | mg |
| Sodium chloride | 1.43 | mg |
| Sodium hydroxide 0.1 n* | q.s. | |
| Hydrochloric acid 0.1 n* | q.s. | |
| Water | ad 1.0 | ml |
| Nitrogen** | q.s. | |

*For adjusting the pH value
**For gassing the solution during preparation and filling
All ingredients are of a quality according to the European Pharmacopoeia (Ph. Eur.).

2. Preparation of a Liquid Formulation for Erythropoietin Having an Active Agent Concentration of 10,000 IE/ml The contents of the individual components per finished syringe correspond to those given in Example 1, with the exception of the erythropoietin content. In this case, the erythropoietin content is 10,000 IE/ml.

The formulations are filled into glass syringes and are stored as finished syringes.

3. Preparation of an EPO Liquid Formulation with a Setup Volume of One Liter An exemplary setup volume of 1 l, with an exemplary protein content of 1,000 μg/ml and an activity of 130,000 IE/mg protein, yields the composition given in the following Table (assumed density of the active agent bulk: 1.008 g/l).

Herein, an agent solution is prepared containing erythropoietin, sodium monohydrogenphosphate dihydrate and sodiumdihydrogenphosphate dihydrate, sodium chloride and water, whose composition is taken into account in the calculation of quantities of the respective components to be weighed in.

| Basic substances | | |
| --- | --- | --- |
| Setup volume* | 1 l = 1,006.7 g | 1 l = 1,006.7 g |
| Agent concentration | 3,333 IE/ml | 10,000 IE/ml |
| Agent content | 25.6 μg/ml | 76.9 μg/ml |
| Agent solution | 25.64 g | 76.97 g |
| Polysorbate 20 | 0.1 g | 0.1 g |
| Sodiumdihydrogenphosphate dihydrate** | 1.43 g | 1.43 g |
| Sodiummonohydrogen-phosphate dihydrate** | 5.6 g | 5.6 g |
| $CaCl_2 \times 2 H_2O$ | 0.01 g | 0.01 g |
| Glycine | 7.5 g | 7.5 g |
| Leucine | 1.0 g | 1.0 g |
| Isoleucine | 1.0 g | 1.0 g |
| Threonine | 0.25 g | 0.25 g |
| Glutamic acid | 0.25 g | 0.25 g |
| Phenylalanine | 0.5 g | 0.5 g |
| Sodium chloride** | 1.43 g | 1.43 g |
| Sodium hydroxide 0.1 n*** | q.s. | q.s. |
| Hydrochloric acid 0.1 n*** | q.s. | q.s. |
| Water** | 984.9 | 984.9 |
| Nitrogen | q.s. | q.s. |

*The setup volume results from the quantity of agent employed and the protein content, which has been determined by means of RP-HPLC.
**Quantity to be weighed in. The content of the excipients of the agent solution is taken into account in quantity calculation.
***The quantity consumed for adjusting the pH value is taken into account in quantity calculation.

4. Method for Preparing the EPO Liquid Formulation

80% of the water for injection purposes are provided in the setup container. The water temperature is monitored, it should lie below 25° C. Subsequently, the correspondingly weighed-in quantities according to the composition given above: sodiumdihydrogenphosphate dihydrate, disodiumhydrogenphosphate dihydrate, calcium chloride, glycine, leucine, isoleucine, threonine, glutamic acid, phenylalanine, and sodium chloride are carefully added while being stirred under nitrogen protection. The solution is stirred until all components are entirely dissolved to form a homogenous solution, at least for 15 minutes, however. Subsequently, the Polysorbate 20 is added to the setup container in form of a separately prepared aqueous solution for injection purposes. The solution is stirred for at least 15 minutes.

For adjusting the pH value, temperature and pH value of the setup are checked in the setup container. The temperature is supposed to lie between 18 and 25° C. The pH value is supposed to lie in a range of 7.0 to 7.4. If the pH value exceeds 7.4, it is adjusted by means of 0.1 n hydrochloric acid. If the pH value lies below 7.0, the correction is performed by means of 0.1 n sodium hydroxide solution. The solution in the setup container is stirred for 10 minutes.

Subsequently to adjusting the pH value, the corresponding quantity of the erythropoietin protein is filled into the setup container.

Once more, temperature (set temperature between 18 and 25° C.) and pH value of the setup are checked. If the pH value exceeds 7.4 or is below 7.0, correction is performed by means of 0.1 n hydrochloric acid and 0.1 n sodium hydroxide solution, respectively.

The solution in the setup container is filled up with water for injection purposes to reach the calculated final weight and is subsequently stirred for at least 15 minutes. If necessary, the pH value has to be corrected once more to lie in a range between 7.0 and 7.4, as stated above. The finished EPO liquid formulation is filled into finished syringes, which are sealed with flask stoppers after filling.

5. Long-Term Stability of the EPO Formulations According to the Present Invention The long-term stability of the EPO formulations according to the present invention has been checked in comparison with the BRP standard as reference. The test is based on the fact that, when storing EPO solutions, degradation and side reactions take place, which can, inter alia, lead to oxidation of methionine and cysteine side chains. Met54 of EPO is particularly often oxidized while forming the respective sulfoxide. Said methionine sulfoxide can be detected with trypsin by means of an RP-HPLC analysis after proteolytic digestion of the EPO. Herein, the proportion of methionine-oxidized species is an indicator for storage stability, i.e. the larger said proportion, the lower the storage stability. Determining the proportion of methionine-oxidized species in the formulations of the present invention at different storage temperatures (2 to 8° C., 25° C., and 40° C.) and different storage periods (6 weeks, 12 weeks, and 6 months), in comparison with formulations according to the prior art, has shown that the formulations according to the present invention have a stability that is comparable to the stability of the liquid formulations according to the prior art.

The invention claimed is:

1. A stable liquid erythropoietin preparation consisting of: erythropoietin, leucine, isoleucine, threonine, glutamic acid, phenylalanine, glycine, calcium chloride, polysorbate, phosphate buffer, and sodium chloride, wherein the pH of the preparation is between 7.0 and 7.4, and wherein the osmolality of the preparation is between 250 mosmol/kg to 300 mosmol/kg.

2. The preparation of claim 1, wherein the polysorbate is Polysorbate 20 or Polysorbate 80.

3. The preparation of claim 2, wherein the concentration of isoleucine and leucine is each between 0.25 to 1.5 g/L, the concentration of glutamic acid is between 0.1 to 0.5 g/L, the concentration of threonine is between 0.1 to 0.5 g/L, the concentration of phenylalanine is between 0.2 to 1.0 g/L, and the concentration of glycine is between 2.0 to 10.0 g/L.

4. The preparation of claim 1, wherein the osmolality is adjusted with sodium chloride.

5. The preparation of claim 4, wherein the concentration of isoleucine and leucine is each between 0.25 to 1.5 g/L, the concentration of glutamic acid is between 0.1 to 0.5 g/L, the concentration of threonine is between 0.1 to 0.5 g/L, the concentration of phenylalanine is between 0.2 to 1.0 g/L, and the concentration of glycine is between 2.0 to 10.0 g/L.

6. The preparation of claim 1, wherein the concentration of isoleucine and leucine is each between 0.25 to 1.5 g/L, the concentration of glutamic acid is between 0.1 to 0.5 g/L, the concentration of threonine is between 0.1 to 0.5 g/L, the concentration of phenylalanine is between 0.2 to 1.0 g/L, and the concentration of glycine is between 2.0 to 10.0 g/L.

7. A method of preparing a storage stable erythropoietin liquid formulation comprising dissolving the components consisting of erythropoietin, the amino acids leucine, isoleucine, threonine, glutamic acid, phenylalanine and glycine as well as calcium chloride, polyoxyethylene sorbitan alkyl ester, sodium chloride in an aqueous buffer, wherein the preparation is not lyophilized in any stage of the process and the formulation is free of urea.

8. The method of claim 7, wherein the components are dissolved in the following order:
   a. calcium chloride
   b. sodium chloride
   c. leucine, isoleucine, threonine, glutamic acid, phenylalanine and glycine,
   d. polyoxyethylene sorbitan alkyl ester and
   e. erythropoietin.

* * * * *